July 18, 1972 C. C. MARSHALL Plant Pat. 3,237
GLADIOLUS
Filed Dec. 28, 1970
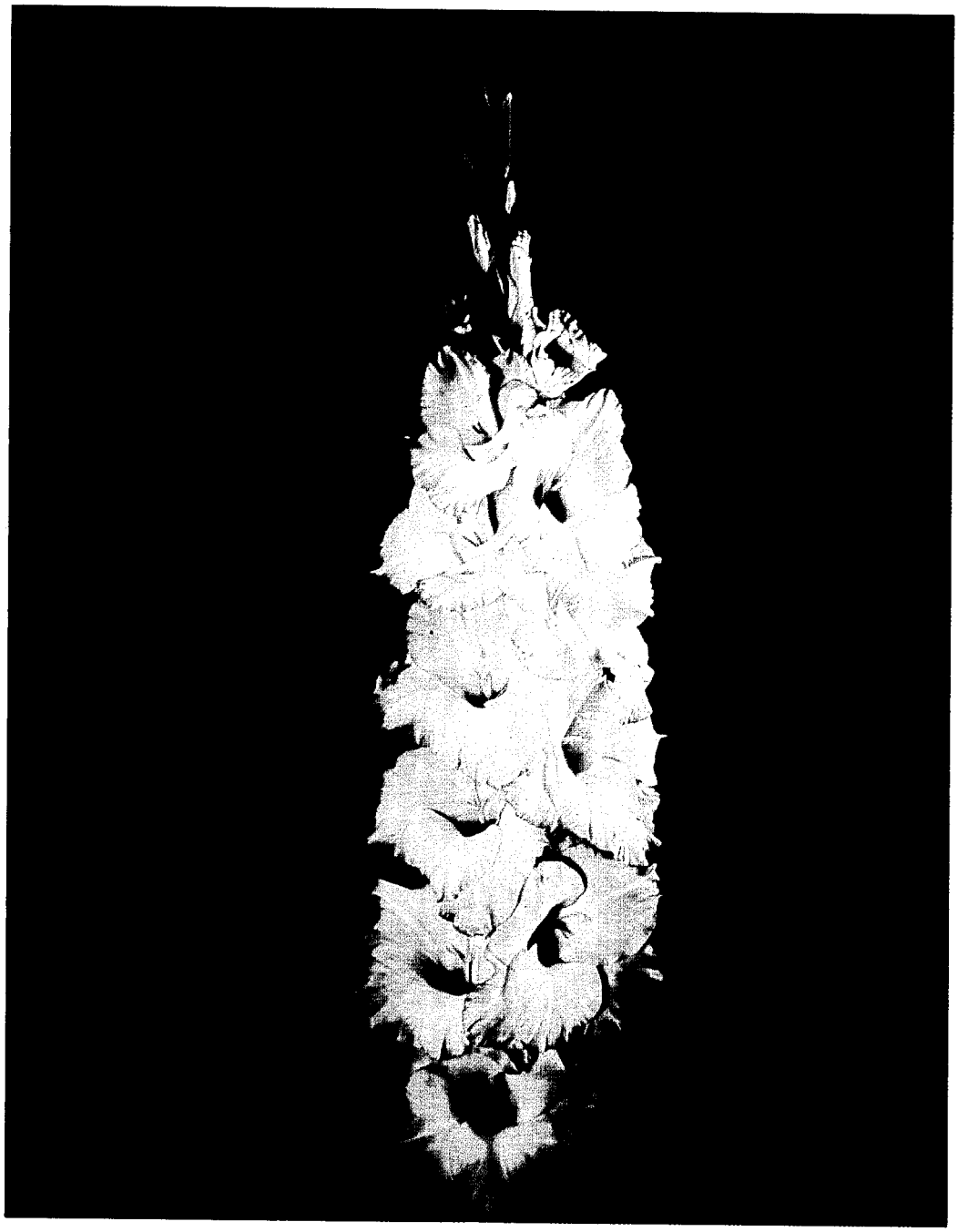

United States Patent Office

Plant Pat. 3,237
Patented July 18, 1972

3,237
GLADIOLUS

Cecil C. Marshall, Hamilton, Ontario, Canada, assignor to Selected Glads, Inc., New Albany, Ind.

Filed Dec. 28, 1970, Ser. No. 102,275
Int. Cl. A01h 5/00
U.S. Cl. Plt.—85 1 Claim This invention relates to a new and distinct variety of gladiolus plant.

This new gladiolus plant was originated by me by crossing a light pink seedling with a lavender seedling, the pink seedling being the seed parent, the lavender seedling being the pollen parent, both being unpatented.

The improved variety resulting from this breeding is evidenced by the following unique combination of characteristics which are outstanding therein and which distinguish my new variety from its parents, as well as from other varieties of which I am aware:

First: Clear pastel lavender coloring light enough to be used in quantity.

Second: The ability to produce sound corms one year after another.

In addition to these major characteristics my variety is also endowed with the following characteristics:

(1) Rugged growth producing unusually strong plants;

(2) Stem freedom from crooking with plants having the ability to stand upright in the field;

(3) Unusually long flowerhead; and (4) Good healthy plants with firm blossoms.

I have asexually reproduced the new variety by cormels through several generations in Ontario, Canada, and succeeding generations have established that the distinguishing characteristics of the variety held true through propagations by plantings derived from cormels.

The accompanying drawing shows a typical specimen of a flower spike of the new variety, with the flowers in varied stages of growth. Some are shown as partially opened buds and others as fully opened buds. The colors depicted are as nearly true as is possible to achieve photographically.

The following is a detailed description of my new variety, with color terminology in accordance with the Horticultural Colour Charts issued by the British Colour Council and the Royal Horticultural Society, except where general color terms of ordinary dictionary significance are obvious.

PLANT

Growth: Strong and healthy; good to excellent propagator.

Blooming habit: Under normal conditions the first bloom appears approximately 85 days, in Canada, after planting.

Stems:

*Form.*—Tall and exceptionally straight.

*Diameter at base.*—About ¾ inch.

*Color at base.*—Light rosy pink—Plate 427/2. Sheaths and stem above the base are medium green.

Foliage: Of moderate length, firm and holds upright in strong plants. The leaves of this variety are medium deep green. The average leaf is 1½ to 1¾ inches wide at the base, grows 30 to 32 inches long, and tapers to a point.

Disease resistance: The variety has been found to be unusually resistant to the usual gladiolus plant diseases of a bacterial, viral or fungoid genesis.

Corms: Mature corms are found, very firm, and rather high crowned with completely covered tough husks. The husk is straw colored at base of bulb—shades of red-purple on top.

*Color of flesh.*—Aureoline or cobalt yellow—Plate 3/4.

FLOWER

Spike:

*Form and size.*—Very straight with bloom spike 52 to 56 inches in height and regularly carrying 18 to 22 buds with flowerhead ranging about 30 inches long.

Bud:

*Size.*—About 3 inches long when opening.

*Opening.*—Eight to ten open at one time with 14 to 16 showing color at one time.

Flower:

*Arrangement.*—In the flowerhead of the new variety florets are regularly placed on the spike.

*Size.*—Individual florets average about 5¾ inches in diameter.

*Form.*—Florets are somewhat round to slightly triangular and ruffled.

*Keeping qualities.*—The flowers keep well and open well in water.

Petals:

*Shape.*—Rounded and lightly frilled.

*Size.*—Upper petals—about 2½ inches wide. Lip petals—about 2 inches wide.

*Aspect.*—Substance is average with the arrangement covering the spike.

*Fragrance.*—None.

*Color.*—At petal edges Plate 433 and Plate 433/2 on lip. Reverse of floret is Plate 433. Sheaths and stem of the flowerhead have a medium green cast.

REPRODUCTIVE ORGANS

Stamens:

*Color.*—Cream—Plate 433/3.

Pistils:

*Color.*—Cream—Plate 433/3.

GROWTH

Locality where grown and observed: Hamilton, Ontario, Canada.

Propagation: Holds its distinguishing characteristics through succeeding propagations from cormels.

This variety resembles "Beverly Ann" (unpatented), but is more of a pastel mauve, larger, taller, has better texture and substance and produces superior corms.

What I claim is:

1. A new and distinct variety of gladiolus plant, substantially as herein shown and described, characterized particularly as to novelty by the unique combination of its clear pastel lavender coloring and the production of sound corms year after year.

No references cited.

ROBERT E. BAGWILL, Primary Examiner